United States Patent [19]

Zaschke et al.

[11] Patent Number: 4,597,892
[45] Date of Patent: Jul. 1, 1986

[54] LIQUID CRYSTALLINE 2-SUBSTITUTED-5-(1-ALKYL-PIPERID-4-YL)-1,3-DIOXANES

[75] Inventors: Horst Zaschke; Hans-Matthias Vorbrodt; Wilfried Fuchs, all of Halle; Adelbert Wiegeleben, Zörbig; Dietrich Demus, Halle, all of German Democratic Rep.

[73] Assignee: VEB Werk fuer Fernsehelektronik im VEB Kombinat Mikroelektronik, Berlin, German Democratic Rep.

[21] Appl. No.: 749,042

[22] Filed: Jun. 26, 1985

[30] Foreign Application Priority Data

Jul. 11, 1984 [DD] German Democratic Rep. ... 265128
Jul. 11, 1984 [DD] German Democratic Rep. ... 265129

[51] Int. Cl.$^4$ .......................... C09K 3/34; G02F 1/13; C07D 407/00; C07D 405/04
[52] U.S. Cl. ..................... 252/299.61; 252/299.5; 350/350 C; 350/350 S; 546/207; 549/370
[58] Field of Search ............... 252/299.5, 299.61; 350/350 R, 350 S; 546/207; 549/370

[56] References Cited

U.S. PATENT DOCUMENTS

| | | | |
|---|---|---|---|
| 4,298,528 | 11/1981 | Setrofer | 252/299.63 |
| 4,344,856 | 8/1982 | Demus et al. | 252/299.63 |
| 4,349,452 | 9/1982 | Osman et al. | 252/299.63 |
| 4,486,332 | 12/1984 | Demus et al. | 252/299.61 |
| 4,537,698 | 8/1985 | Sucrow et al. | 252/299.61 |

FOREIGN PATENT DOCUMENTS 3220155 12/1983 Fed. Rep. of Germany ................. 252/299.61

OTHER PUBLICATIONS

Karamysheva, L. A., et al., Advances in Liq. Cryst. Res. and Appl., vol. 2, Bata, Lajos, Ed., Pergamon Press, London, pp. 997–1002 (1981).

Primary Examiner—Teddy S. Gron
Attorney, Agent, or Firm—Jordan and Hamburg

[57] ABSTRACT

2-Substituted-5-(1-alkyl-piperid-yl)-1,3-dioxanes of the formula I

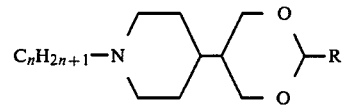

wherein
R =

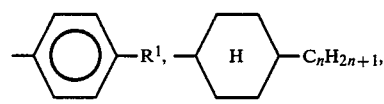

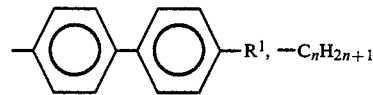

$R^1 =$ —$C_nH_{2n+1}$, —$OC_nH_{2n+1}$, —$OOCC_nH_{2n+1}$, —$COC_nH_{2n+1}$, —$OOCOC_nH_{2n+1}$, —F, —Cl, —Br, —I, —$NO_2$, —CN —$(CH_2)_2CN$,

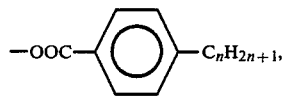

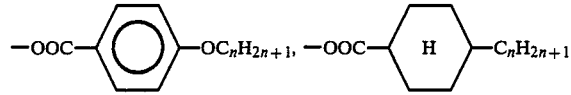

and n=1 to 10, are novel liquid crystalline compounds, which can be produced in high yields by means of reacting 2-(1-alkyl-piperid-4-yl)-propane-1,3-diols with aldehydes in the presence of acid catalysts, such as p-toluenesulfonic acid, mineral acids and Lewis acids. Because of their high thermal and chemical stability, which is also transferred to mixtures, the compounds of the formula I are very well suited for utilization in optoelectronic displays.

14 Claims, No Drawings

LIQUID CRYSTALLINE 2-SUBSTITUTED-5-(1-ALKYL-PIPERID-4-YL)-1,3-DIOXANES

The invention relates to liquid crystalline 2-substituted-5-(1-alkyl-piperid-4-yl)-1,3-dioxanes of the general formula I

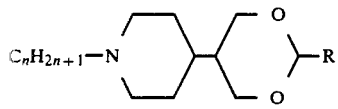

wherein
R = one of

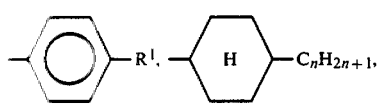

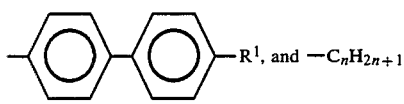

$R^1$ = one of —$C_nH_{2n+1}$, —$OC_nH_{2n+1}$, —$OOCC_nH_{2n+1}$, —$COC_nH_{2n+1}$, —$OOCC_nH_{2n+1}$, —F, —Cl, —Br, —I, —$NO_2$, —CN, —$(CH_2)_2CN$,

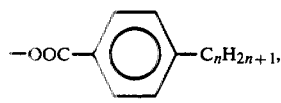

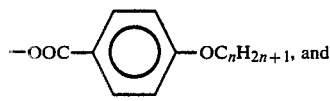

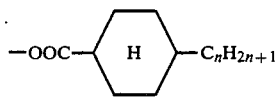

and
n = 1 to 10,
a method for the production of these dioxanes and the utilization of the nematic liquid crystals as an additive in mixtures for opto-electronic displays, which are being used for the modulation of incident or transmitted light, as well as for the rendition of numbers, symbols or images.

Because of their advantageous physical characteristics, liquid crystalline substituted 1,3-dioxanes are being used in electrooptical indication systems for the rendition of numbers and symbols. The all-trans 5-(4-alkyl-cyclohexyl)-2-(4-cyanophenyl)-1,3-dioxanes have thereby proven to be especially advantageous; DD Pat. No. 207,308. During the synthesis of the therefor required trans 2-(4-alkyl-cyclohexyl)-propane-1,3-diols, are created in considerable amounts the cis-isomer compounds, which are not suitable as synthesis components for liquid crystalline dioxane compounds. Thus, a large amount of the starting material is lost and the total yield of liquid crystalline compounds is unsatisfactory.

So far, there are no known substitutes for the 5-piperid-4-yl-1,3-dioxanes, and there are no described methods for their production.

The liquid crystals used in opto-electronic passive components have to possess definite characteristics with regard to melting point, clarification point, electro-optical threshold voltage, electrical conductivity, optical anisotropy, viscosity, as well as thermal and chemical stability.

So far, there exists no pure substance, which could even approximately fulfill these requirements. Therefore, mixtures are used without exception, whereby their characteristics are adjusted by means of specifically selecting the components for the intended particular purpose of utilization. In order to be able to modify the characteristics of the mixtures in a targeted way, there are always required new substances having different properties.

One requirement, which is difficult to meet in certain classes of substances, is the necessary stability of the substances or the mixtures thereof.

The object of the invention is to provide derivatives of the 1,3-dioxanes of the formula I which have a high stability in addition to favorable liquid crystalline properties and which simultaneously stabilize mixtures of other liquid crystalline substances, as well as a method of production, which permits a synthesis at a high yield and of a good purity.

It has been found that liquid crystalline 2-substituted-5-(1-alkyl-piperid-4-yl)-1,3-dioxanes of the general formula I can be produced at high yields by means of reacting the 2-(1-alkyl-piperid-4-yl)-propane-1,3-diols V with aldehydes in the presence of acid catalysts, such as p-toluenesulfonic acid, mineral acids and Lewis acids. In contrast to the normal acetalizations, for the synthesis of the compounds I, at least equimolar quantities of catalyst are required. Unlike in other syntheses of cyclohexyldioxane derivatives, there do not result isomers with non-liquid crystalline characteristics.

The new diols V utilized for the synthesis of I can be obtained in accordance with the following scheme:

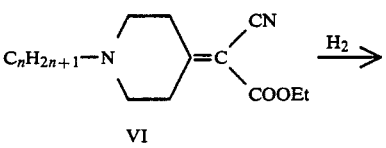

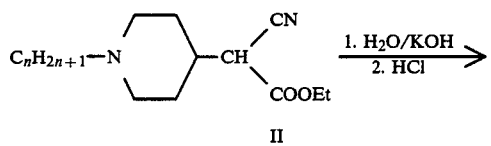

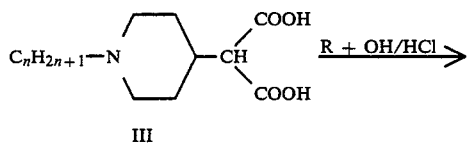

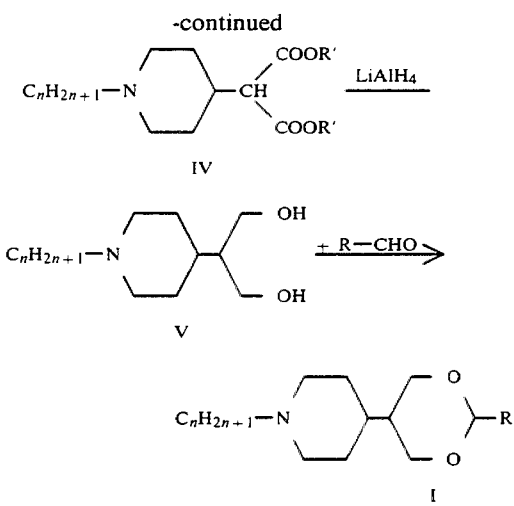

(1-alkyl-piperid-4-ylene)-cyanoacetic ester VI is hydrogenated in the presence of hydrogenation catalysts at room temperature under normal pressure into (1-alkyl-piperid-4-yl)-cyanoacetic ester II. II is saponified with aqueous alkali into (1-alkyl-piperid-4-yl)-malonic acid III, which is subsequently esterified with an alcohol. The reduction of the ester IV with complex hydrides supplies after a basic work up the 2-(1-alkyl-piperid-4-yl)-propane-1,3-diol V. IV or esters thereof are also obtainable in a single-vessel reaction by means of reacting II with alkanol/mineral acids.

The compounds according to the invention of the general formula I possess liquid crystalline properties and, because of their high thermal and chemical stability, which is transferred to the mixtures, are very well suited for utilization in opto-electronic displays.

In particular, mixtures containing the up to now known liquid crystalline dioxane derivatives in quantities of 20 to 80% are stabilized by adding the substances according to the invention. The new compounds are colorless and have high clarification temperatures.

The following example will more closely explain the production of the compounds according to the invention.

EXAMPLE

For the production of the (1-butyl-piperid-4-yl)-cyanoacetic ester II, in 250 ml EtOH, 25 g (0.1 mol) (1-butyl-piperid-4-ylene)cyanoacetic ester VI, is hydrogenated in the presence of 2 g Pd/C (5% Pd) at room temperature and normal pressure, with the use of a shaking apparatus, until $H_2$ absorption is completed.

Clarification point: 155° C. (67 Pa)
Yield: 20 g (80% of the theoretical)

25.2 g (0.1 mol) (1-butyl-piperid-4-yl)-cyanoacetic ester II and 16.8 g (0.3 mol) KOH are heated in 100 ml water for 10 hours with reflux. After cooling the reaction mixture, 30 ml (0.3 mol) concentrated HCl are added. The free (1-butyl-piperid-4-yl)-malonic acid III crystallizes out of water after reducing the reaction mixture.

Solidification point: 195° C. (decomposition)
Yield: 20 g (80% of theoretical)

12 g (0.05 mol) (1-butyl-piperid-4-yl)-malonic acid III is dissolved in 100 ml abs. EtOH and dry HCl gas is passed thereinto until saturation occurs. Subsequently, it is heated with reflux for another 4 hours. The main quantity of the alcohol is distilled off at the rotary evaporator, whereafter the free base is set free with aqueous $K_2CO_3$ solution. The product is absorbed in ether, the ether is washed twice with water. After drying with $Na_2SO_4$, the ether is distilled off in a rotary evaporator and the residue is fractionally distilled under vacuum.

Clarification point: 138° C. (40 Pa)
Yield: 10 g (78% of theoretical)

(1-butyl-piperid-4-yl)-malonic acid diethyl ester IV 30 g (0.1 mol) (1-butyl-piperid-4-yl)-malonic acid diethyl ester IV is mixed with an equal volume of abs. ether and dropwise added to 5.1 g (0.15 mol) $LiAlH_4$ in 200 ml abs. ether. After this has been added, it is heated for 10 hours with reflux. Then it is decomposed with the barely required amount of water and the precipitated hydroxide is filtered off. The hydroxide is washed with ether, and the combined ether phases are reduced in a rotary evaporator. The residue, the 2-(1-butyl-piperid-4-yl)-propane-1,3 diol V, is recrystallized from acetone.

Solidification point: 82° C.
Yield: 15 g (70% of theoretical)

2.15 g (0.01 mol) 2-(1-butyl-piperid-4-yl)-propane-1,3-diol V and 1.31 g (0.01 mol) p-cyanobenzaldehyde are heated in 50 ml benzene in the presence of 2.1 g (0.011 mol) p-toluenesulfonic acid (monohydrate) for 2 hours in a water separator. The cooled reaction mixture is washed with 100 ml 5-% $K_2CO_3$ solution and water and is dried with $Na_2SO_4$. After decanting the solvent, the solid matter obtained, the 2-(4-cyanophenyl)-5-(1-butyl-piperid-4-yl)-1,3-dioxane I is recrystallized from methanol.

Yield: 2 g (71% of theoretical)

Further compounds according to formula I indicated in the following chart were obtained in an analogous way:

TABLE

| Comp. | n | R | K | S | N | I |
|---|---|---|---|---|---|---|
| I.1. | 3 | NC—⟨O⟩— | .101 | — | .181 | . |
| I.2. | 3 | O₂N—⟨O⟩— | .118 | — | .141 | . |
| I.3. | 4 | NC—⟨O⟩— | .82 | — | .169 | . |
| I.4. | 4 | O₂N—⟨O⟩— | .101 | — | .137 | . |
| I.5. | 4 | C₆H₁₃—⟨H⟩— | .42 | .204 | — | . |
| I.6. | 4 | C₄H₅O—⟨O⟩— | .20 | .175 | — | . |
| I.7. | 4 | C₅H₁₁O—⟨O⟩— | .30 | .169 | — | . |

TABLE-continued

I

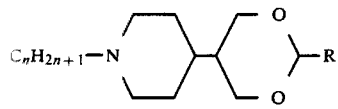

| Comp. | n | R | K | S | N | I |
|---|---|---|---|---|---|---|
| I.8. | 4 | C₆H₁₃—⟨O⟩— | .105 | .165 | — | . |
| I.9. | 4 | C₆H₁₃— | .35 | .83 | — | . |
| I.10. | 4 | C₂H₅O—⟨O⟩—COO—⟨O⟩— | .131 | — | .291 | . |
| I.11. | 6 | NC—⟨O⟩— | .89 | — | .163 | . |
| I.12. | 6 | O₂N—⟨O⟩— | .77 | .102 | .132 | . | wherein
K = solid crystalline
S = smectic
N = nematic
I = liquid isotropic

The following data are intended for the characterization of the substances according to the invention with respect to their utilization in nematic liquid crystalline mixtures.

The thermal stability has been examined for substances I.3 and I.5.

1. The substances were treated for 14 hours at 80° C. on the "Boethius" heating table. For the substance I.5., there did not result a clarification point reduction during this period; substance I.3. showed a clarification point reduction of 3° K.

2. A treatment for 22 hours at 100° C. of the samples of the substance I.5. did not show any clarification point reduction; for substance I.3., there resulted a clarification point reduction of 50° K.

The good electro-optical properties of mixtures containing the substances according to the invention will be demonstrated by the following results.

As liquid crystalline fundamental mixture was used the mixture "Mi 14" consisting of 3 components of the compound class

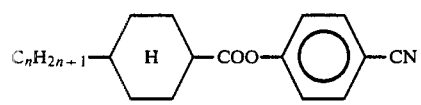

wherein
n=3; 34.5 mol %
n=4; 31.0 mol %
n=5; 34.5 mol %

The change of the electro-optical parameters in Schadt-Helfrich type cells is indicated.

| Mi 14 (mol %) | Substance No. | (mol %) | $U_o$ (V) | $\tau_E^{50}$(ms) $\tau U = 2 U_o$ in ref. to d = 10 μm | $\tau_A^{50}$ | Melting temperature °C. | Clarification temperature °C. |
|---|---|---|---|---|---|---|---|
| 100 | — | — | 1.3 | 101 | 35 | | 72 |
| 90 | I.3. | 10 | 1.2 | 232 | 46 | | 81.5 |
| 90 | I.5. | 10 | 1.3 | 62 | 11 | | 81 |

$U_o$ = Threshold voltage at 20° C., 500 Hz
$\tau_E^{50}$ = Switching-on period at 50% intensity change, 20° C., 500 Hz
$\tau_A^{50}$ = Decay period at 50% intensity change, 20° C., 500 Hz
U = Operating voltage
d = Thickness of layer In the determination of the melting enthalpies by means of DSC, the following enthalpy values have been determined:

| Substance No. | $\Delta F^H$ (kJ/mol) |
|---|---|
| I.3. | 26.4 |
| I.5. | 28.2 |

$\Delta F^H$ = Melting enthalpy

The comparatively low values of the melting enthalpies result in strong depressions of the melting temperatures in mixtures, so that this leads to the highly desirable mixtures of low melting temperatures and low operating temperatures.

For the demonstration of the change of the clarification point, to a mixture of dioxane derivatives of the composition

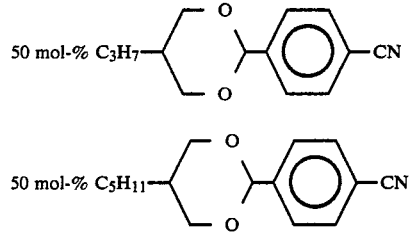

of the clarification point of 43° C., 20 mol-% substance I according to the invention was added.

The obtained clarification point increases are indicated in the following chart:

| added substance No. | clarification point °C. |
|---|---|
| I.3. | 68.0 |
| I.5. | 75.5 |

For the substance I.3., the following values have been determined for the dielectrical anisotropy and viscosity:
Dielectrical anisotropy $\Delta\epsilon = +12$ at 82° C.
Viscosity $\eta_2 = 154$ cP at 25° C. (extrapolated)

We claim:
1. Liquid crystalline 5-(1-alkyl-piperid-4-yl)-1,3-dioxanes of the general formula I

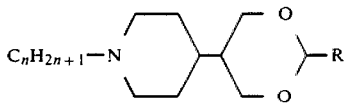

wherein
R = one of

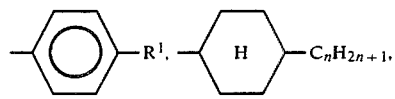

$R^1$ = one of  —$C_nH_{2n+1}$, —$OC_nH_{2n+1}$, —$OOCC_nH_{2n+1}$, —$COC_nH_{2n+1}$, —O-COO$C_nH_{2n+1}$, —F, —Cl, —Br, —I, —$NO_2$, —CN, —$(CH_2)_2CN$,

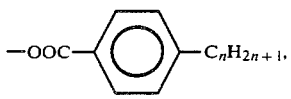

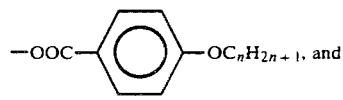

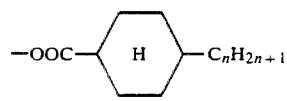

and
n = 1 to 10.

2. Liquid crystalline substances of claim 1, wherein n = 3 and R =

3. Liquid crystalline substances of claim 1, wherein n = 3 and R =

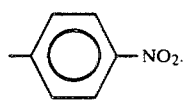

4. Liquid crystalline substances of claim 1, wherein n = 4 and R =

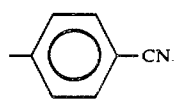

5. Liquid crystalline substances of claim 1, wherein n = 4 and R =

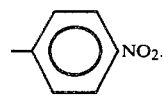

6. Liquid crystalline substances of claim 1, wherein n = 4 and R =

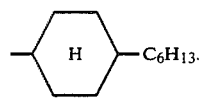

7. Liquid crystalline substances of claim 1, wherein n = 4 and R =

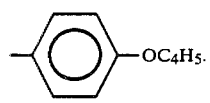

8. Liquid crystalline substances of claim 1, wherein n = 4 and R =

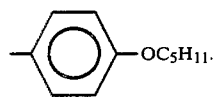

9. Liquid crystalline substances of claim 1, wherein n = 4 and R =

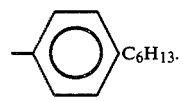

10. Liquid crystalline substances of claim 1, wherein n = 4 and R = $C_6H_{13}$—.

11. Liquid crystalline substances of claim 1, wherein n = 4 and R =

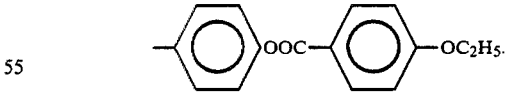

12. Liquid crystalline substances of claim 1, wherein n = 6 and R =

13. Liquid crystalline substances of claim 1, wherein n = 6 and R =

14. In an opto-electronic display containing at least one nematic liquid crystalline substance, the improvement in which the at least one nematic liquid crystalline substance is selected from the group consisting of nematic liquid crystalline substances according to claim 1, mixtures of nematic liquid crystalline substances according to claim 1, and mixtures of at least one nematic liquid crystalline substance according to claim 1 with at least one other nematic crystalline substance.

* * * * *